United States Patent [19]

Scott

[11] Patent Number: 4,822,935
[45] Date of Patent: Apr. 18, 1989

[54] HYDROGASIFICATION OF BIOMASS TO PRODUCE HIGH YIELDS OF METHANE

[76] Inventor: Donald S. Scott, 382 Arden Place, Waterloo, Ontario, Canada, N2L 2N7

[21] Appl. No.: 89,397

[22] Filed: Aug. 26, 1987

[30] Foreign Application Priority Data

Aug. 26, 1986 [CA] Canada .................................. 516826

[51] Int. Cl.$^4$ ................................................ C07C 1/00
[52] U.S. Cl. ..................................... 585/240; 252/373; 423/652; 585/242
[58] Field of Search ................. 585/240, 242; 252/373; 423/652

[56] References Cited

U.S. PATENT DOCUMENTS

| 4,102,938 | 7/1978 | Rao | 585/240 |
| 4,300,009 | 11/1981 | Haag et al. | 585/240 |
| 4,618,736 | 10/1986 | Benn et al. | 585/240 |
| 4,652,686 | 3/1987 | Coenen et al. | 585/240 |

Primary Examiner—Curtis R. Davis
Attorney, Agent, or Firm—Daryl W. Schnurr

[57] ABSTRACT

A process for hydrogasification of biomass to produce high yields of methane utilizes a reactor capable of carrying out rapid pyrolysis. Biomass particles, hydrogen, particles of a suitable catalyst that has both cracking and hydrogenation activity, and heat are introduced into said reactor. Pyrolysis is carried out in a hydrogen-rich atmosphere under the following conditions: (a) a temperatue ranging from 500° C. to 550° C.; (b) a pressure equal to or greater than one atmosphere; (c) a gas residence time not exceeding two seconds; (d) a biomass particle residence time at least as long as the gas residence time; (e) a biomass particle size not exceeding 2 mm. The methane-rich product gas is then recovered. Conversion of carbon to methane of 69% has been attained using the process of the present invention.

12 Claims, 2 Drawing Sheets

Schematic of Integrated Gasification Process for Production Methane-Rich Gas and/or Synthesis Gas from Wood

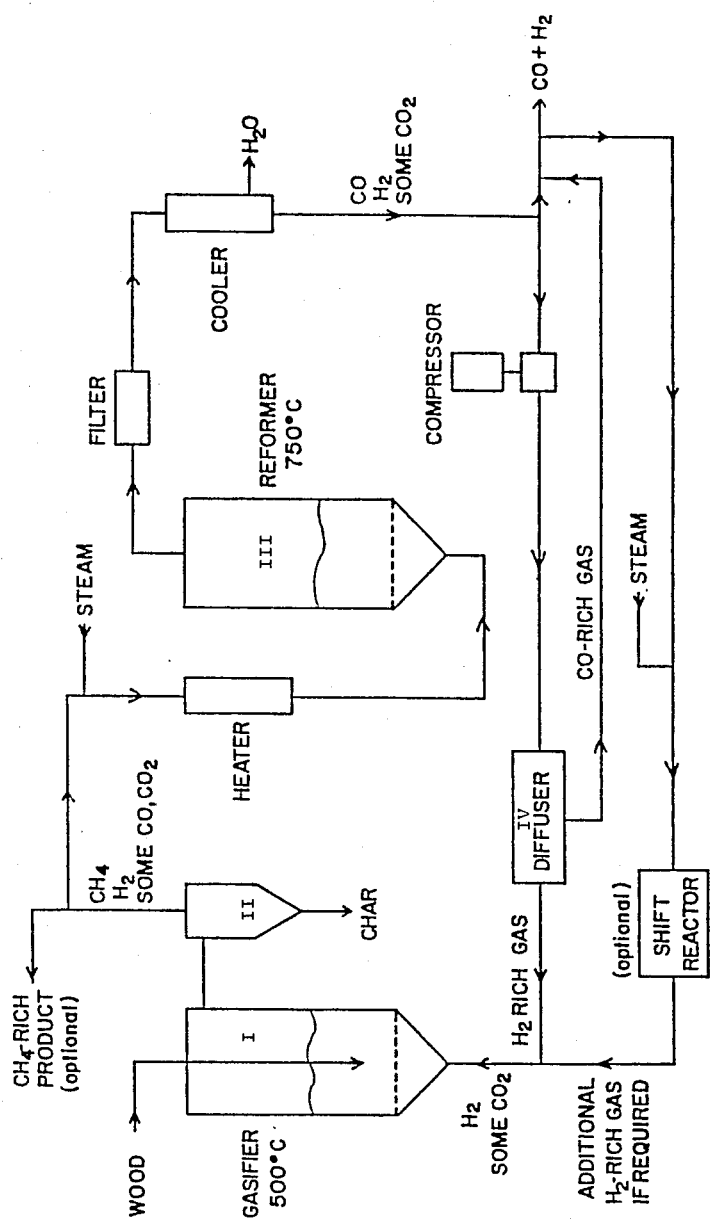
Figure 1 Schematic of Integrated Gasification Process for Production Methane-Rich Gas and/or Synthesis Gas from Wood

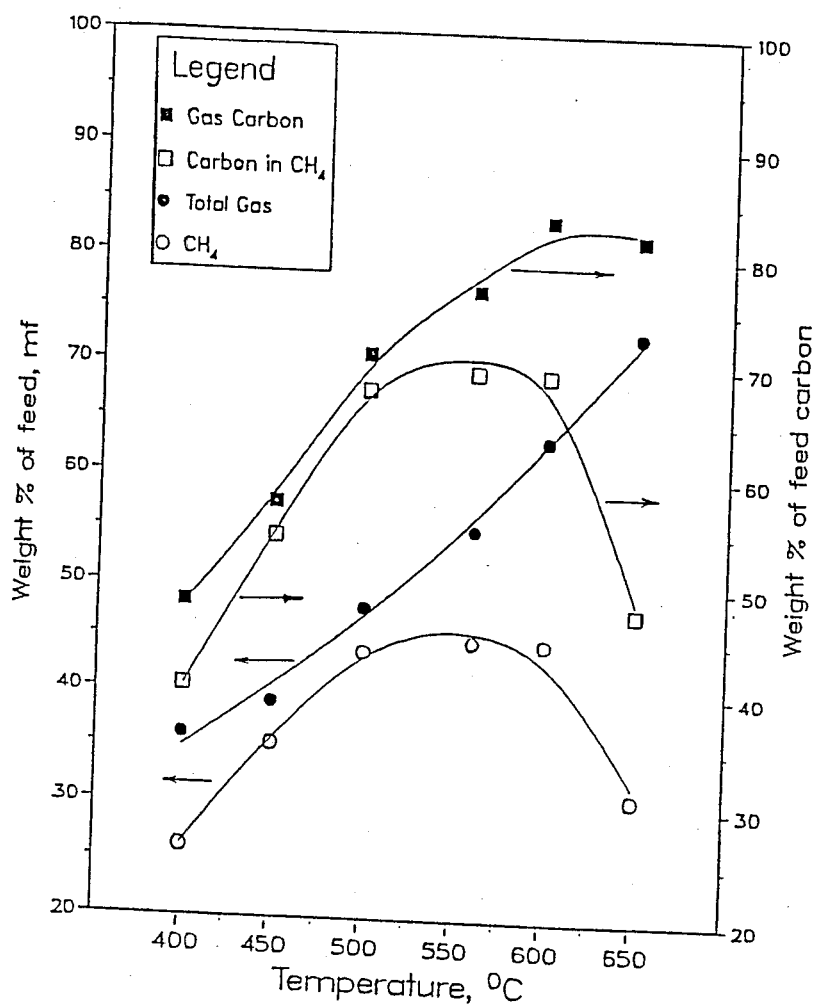
Fig. 2 Effect of Temperature on Gas and CH4 Production Lab (2) Ni Cat., H2 Atmosphere, 0.44 sec.

HYDROGASIFICATION OF BIOMASS TO PRODUCE HIGH YIELDS OF METHANE

BACKGROUND OF THE INVENTION

1. Field of the Invention

This invention relates to a process of hydrogasification of biomass for producing high yields of methane, said process utilizing a hydrogen-rich atmosphere in a reactor capable of carrying out rapid pyrolysis.

2. Description of the Prior Art

It is known to convert biomass material to gaseous products. The main components of any such conversion are carbon monoxide, carbon dioxide, hydrogen and methane. Carbon dioxide is usually an undesirable by-product. One known method is to use air or oxygen-enriched air for heat for the gasification reaction. It is supplied by oxidation of part of the biomass with the oxygen in the air. Unfortunately, when air or oxygen-enriched air is used, inert nitrogen is introduced into the gasifier and the product gases are thereby diluted. This dilution is undesirable for many applications. A further known method involves the use of oxygen alone. This method results in a product gas which is essentially free of nitrogen but it contains some carbon dioxide. The major disadvantage of this process is that an air separation plant is required to supply the oxygen. A further known method is to use an atmosphere of steam-oxygen. However, this method also requires an oxygen plant and high gasification temperatures. Still further, steam alone can be used to react with biomass or steam can be used along with a solid catalyst. This method requires high temperatures, thereby making it difficult to use some catalysts and also making the process more expensive to operate. Also, this process can be limited in the range of gas compositions that can be produced.

SUMMARY OF THE INVENTION

It is an object of the present invention to provide a process whereby a high yield of methane can result from the direct pyrolysis of biomass in a hydrogen atmosphere.

In accordance with the present invention, a process of hydrogasification of biomass for producing high yields of methane comprises introducing biomass particles, hydrogen, particles of a suitable catalyst that has both cracking and hydrogenation activity and heat into a reactor capable of carrying out rapid pyrolysis. The biomass particles are mixed with said catalyst particles in said reactor in a hydrogen-rich atmosphere. Pyrolysis is carried out under the following reaction conditions:
(a) a temperature ranging from substantially 450° C. to substantially 600° C.;
(b) a pressure at least as high as substantially one atmosphere;
(c) a gas residence time not exceeding substantially 5 seconds;
(d) a biomass particle residence time at least as long as the gas residence time;
(e) a biomass particle size not exceeding substantially 2 mm;
Methane rich product gas so formed is recovered.

BRIEF DESCRIPTION OF THE DRAWINGS

FIG. 1 is a schematic flow diagram for the production of methane-rich gas and/or synthesis gas from wood in accordance with the present invention; and FIG. 2 is a graph showing the effect of temperature on gas and methane production using a process in accordance with the present invention.

DESCRIPTION OF A PREFERRED EMBODIMENT

Referring to FIG. 1 generally there is shown one embodiment of the process of the present invention. It can be seen that a gasifier or reactor is one of the most important parts of the process. The reactor must have a configuration and mode of operation which causes intimate and rapid mixing of biomass particles and catalyst particles in an atmosphere within the reactor. Further, the reactor must permit the addition of or removal of heat. Preferably the reactor is a fluidized bed reactor but other types of reactors may be suitable.

Suitable fluidized bed reactors are described by Donald S. Scott, et al. in the Canadian Journal of Chemical Engineering, 1984, Volume 62, pp. 404–412 and Industrial and Engineering Chemistry Process Design and Development, 1985, Volume 24, pp. 581–588.

Any solid catalyst that has particles with both cracking and hydrogenation capabilities may be suitable in the process of the present invention.

If we use wood as an example and assume that the overall atomic composition of wood is represented by the approximate formula $C_6H_9O_4$, then the hydrogasification reaction can be written ideally as:

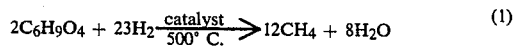

$$2C_6H_9O_4 + 23H_2 \xrightarrow[500°\text{C.}]{\text{catalyst}} 12CH_4 + 8H_2O \qquad (1)$$

The source of the hydrogen can vary. However, the hydrogen is preferably obtained by steam reforming a part of the product gas from the reaction, said product gas being high in methane, in accordance with the following equation:

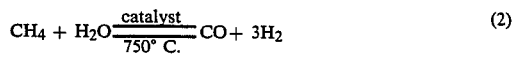

$$CH_4 + H_2O \xrightarrow[750°\text{C.}]{\text{catalyst}} CO + 3H_2 \qquad (2)$$

The method of steam reforming the product gas to produce hydrogen is well known. If we assume that all of the product from reaction (1) undergoes the steam reforming reaction, then reaction (2) can be rewritten as follows:

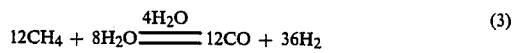

$$12CH_4 + 8H_2O \xrightarrow{4H_2O} 12CO + 36H_2 \qquad (3)$$

After the steam reforming reaction is carried out, a portion of the product gases from reaction (3) are then separated into a hydrogen-rich stream and a carbon monoxide-rich stream in accordance with the following:

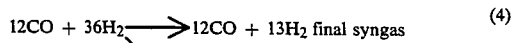

$$12CO + 36H_2 \longrightarrow 12CO + 13H_2 \text{ final syngas} \qquad (4)$$

$$\searrow 23H_2 \text{ - recycle to hydrogasification reactor}$$

Overall, the effect of this three-stage process is to produce synfuel, or a methane-rich fuel gas as represented by:

$$2 C_6H_9O_4 + 4 H_2O \rightarrow 12 CO + 13 H_2 \quad (5)$$

Reaction (5) shows that the process converts biomass and its self-contained moisture (plus any additional moisture required), to syngas with no other inputs required.

Preferably, the process should be carried out under the following conditions:
(a) a temperature ranging from substantially 450° C. to substantially 600° C.;
(b) a pressure at least as high as substantially one atmosphere;
(c) a gas residence time not exceeding substantially 5 seconds;
(d) a biomass particle residence time at least as long as the gas residence time.

Preferably, the biomass has a moisture content not exceeding substantially 30% by weight. Still more preferably, the gas residence time does not exceed substantially two seconds. Further, the temperature preferably ranges from substantially 500° C. to substantially 550° C.

Referring to FIG. 1 in greater detail, reactor I is the gasifier or pyrolysis reactor or hydrogasification reactor. Preferably, this reactor is a fluidized bed and is fed with biomass having a particle size of preferably less than 2 mm and any moisture content which can be readily fed. A moisture content of 20% by weight or less is preferable.

The hydrogasification reactor can be operated at any convenient pressure and at temperatures ranging from substantially 450° C. to substantially 650° C., but the highest methane yields will be obtained at temperatures ranging from substantially 500° C. to substantially 550° C. when the pressure is substantially atmospheric. One example of a suitable fluid bed catalyst is a γ-alumina support containing metallic nickel with a preferable nickel content of at least 8%. However, other suitable catalysts in which the support has a moderately acidic character and the metal is from Group VIII of the periodic Table may be used. Supports with strong cracking activity, for example, silica-alumina, are not as desirable because the pyrolysis reaction can be unstable and high cracking activity can form undesirable amounts of secondary carbon on the catalyst surface.

The preferred ratio of weight of feed per hour to weight of catalyst is preferably less than two, but ratios having values up to seven have been used to produce less than optimal results. The optimal feed to catalyst ratio will differ for each catalyst, but the preferred value of less than two hrs$^{-1}$ gives high methane yields with a minimum formation of secondary carbon for nickel on an alumina support.

From FIG. 2 and Table 1, the results of hydrogasification tests using the process of the present invention as a function of temperature can be seen. At temperatures ranging from 500° C. to 600° C., a maximum conversion of carbon to methane (approx. 69%) is obtained with a gas selectivity ranging from 83% to 95%. If high yields of total gases are desired, a higher temperature can be used but then the methane yields will decrease because of equilibrium considerations involving the reaction between methane and water. The higher the moisture content of the wood, the lower the yield of methane at higher temperatures (i.e. above 600° C.) because of the high water content of the product gas.

The reason that the process of the present invention can obtain high conversions of biomass to methane is due to the fact that the reaction occurs at lower temperatures than for other gasification processes and usually at a lower water content. As shown in FIG. 1, the products leaving the hydrogasification reactor I pass through a cyclone II where char or any catalyst particles are removed. The gases and tar vapours then pass through the steam reformer III after the water content has been adjusted. In the steam reformer, the methane, oil vapour and any hydrocarbon gases, such as ethylene or ethane are reacted with steam over a catalyst at higher temperatures, for example, 750° C., to cause the reaction set out in equation (2) to occur. If not all the methane-rich gas from the hydrogasification reactor I is to be converted to synthesis gas, then a part may be withdrawn as product before entering the steam reformer II as shown in FIG. 1. If the only product desired is a methane-rich gas, then only a sufficient part of the hydrogasification product is passed through the steam reformer to generate the hydrogen-rich steam required for the hydrogasification reaction {see equation (1)} in reactor I.

After leaving the steam reformer, the gases are cooled and condensed water is removed for reuse. The gases are compressed and sent to a separation process IV for separation into a hydrogen-rich stream and a carbon monoxide-rich stream. Any conventional technology can be used for this separation, for example, cryogenic separation or diffusional separation. The diffusional method uses known membrane technology and is likely to be the most economical.

The hydrogen-rich stream is returned to the hydrogasification reactor and the carbon monoxide-rich stream is the synthesis gas product. When synthesis gas is the desired final product, only a portion of the product stream from the steam reformer III needs to be sent to the separation unit IV in an amount which will preserve the hydrogen balance of the process. If the methane-rich product from the hydrogasification reactor I is the desired product, then all the gases from the steam reformer III are separated into a hydrogen-rich and a carbon monoxide-rich stream. Further, this carbon monoxide-rich stream can be further reacted over a catalyst by a "shift" reaction as set out in equation (6) to yield additional hydrogen. This method is also conventional.

$$CO + H_2O \rightleftharpoons CO_2 + H_2 \quad (6)$$

If all the product gas from the reformer III is separated, and all the carbon monoxide-rich stream undergoes the reaction in equation (6), then the process becomes a means of producing hydrogen from biomass. The process of the present invention allows biomass to be converted to either a methane-rich gas or a synthesis gas, using no additional reactants, except water, if insufficient water is present in the biomass feed. Flexibility exists as to the choice of product and it is even possible to produce a methane-rich gas and a synthesis gas simultaneously. If desired, a hydrogen-rich gas as well as a methane-rich gas and synthesis gas can be produced simultaneously. The process has a further advantage in that it can be carried out at atmospheric pressure and low temperatures using direct catalytic hydrogasification. With previous reactions, the temperature ranges from 700° C. to 1100° C. While process of the present invention proceeds satisfactorily at one atmosphere absolute pressure, pressures higher than one atmosphere absolute can be used. Higher pressures will be advantageous in increasing the yields of methane.

acidic character and a metal selected from Group VII of the Periodic Table.

TABLE 1

Yields of gasification products with temperature
Lab(2) Ni cat., 17% Nickel, Res. Time 0.43–0.45 s

| | RUN NO. | | | | | |
|---|---|---|---|---|---|---|
| | G-20 | G-15 | G-14 | G-13 | G-18 | G-21 |
| Temperature, C. | 400 | 450 | 500 | 560 | 600 | 650 |
| F/C RATIO, 1/hr | 1.83 | 1.19 | 1.45 | 1.41 | 1.18 | 1.66 |
| TOTAL YIELD OF COMPONENTS, (% WT. OF FEED, MF) | | | | | | |
| CO | 3.85 | 1.86 | 2.10 | 5.32 | 10.80 | 31.66 |
| $CO_2$ | 5.01 | 1.71 | 1.89 | 5.00 | 7.48 | 10.13 |
| $CH_4$ | 26.13 | 35.21 | 43.71 | 44.78 | 44.70 | 30.88 |
| $C_2H_4$ | 0.21 | 0.03 | 0.02 | 0.00 | 0.09 | 0.00 |
| $C_2H_6$ | 0.18 | 0.03 | 0.01 | 0.00 | 0.05 | 0.01 |
| $C_3$ | 0.19 | 0.12 | 0.02 | 0.00 | 0.07 | 0.00 |
| $C_4+$ | 0.40 | 0.05 | 0.13 | 0.00 | 0.05 | 0.16 |
| Total Gas | 35.96 | 39.01 | 47.87 | 55.10 | 63.24 | 72.84 |
| Char | 20.34 | 14.08 | 12.44 | 9.01 | 7.27 | 6.97 |
| Tar | 19.68 | 14.30 | 4.78 | 1.33 | 3.35 | 1.37 |
| Water | 27.68 | 36.00 | 46.45 | 41.63 | 33.92 | 19.37 |
| TOTAL YIELD | 103.66 | 103.39 | 111.54 | 107.07 | 107.78 | 100.55 |
| REFORMABLE GASES | 30.94 | 37.30 | 45.98 | 50.10 | 55.76 | 62.71 |
| TOTAL GAS CARBON | 48.28 | 57.45 | 70.82 | 76.76 | 83.33 | 81.72 |
| CARBON IN $CH_4$ | 40.40 | 54.46 | 67.60 | 69.25 | 69.14 | 47.76 |
| SCM $CH_4$/FEED | 0.39 | 0.53 | 0.66 | 0.68 | 0.68 | 0.47 |
| REFORMABLE C IN GAS | 94% | 98% | 98% | 96% | 95% | 93% |
| SELECTIVITY FOR $CH_4$ | 84% | 95% | 95% | 90% | 83% | 58% |
| HHV GAS/FEED | 0.79 | 1.02 | 1.26 | 1.30 | 1.34 | 1.05 |

I claim:

1. A process of hydrogasification of biomass for producing high yields of methane, said process comprising introducing biomass particles, hydrogen, particles of a catalyst that has both cracking and hydrogenation activity and heat into a reactor capable of carrying out rapid pyrolysis, mixing said biomass particles with said catalyst particles in said reactor in a hydrogen-rich atmosphere, carrying out said pyrolysis under the following reaction conditions:
   (a) a temperature ranging from substantially 450° C. to substantially 600° C.;
   (b) a pressure at least as high as substantially one atmosphere;
   (c) a gas residence time not exceeding substantially 5 seconds;
   (d) a biomass particle residence time at least as long as the gas residence time;
   (e) a biomass particle size not exceeding substantially 2 mm;
and recovering methane rich product gas so formed.

2. A process as claimed in claim 1 wherein the biomass has a moisture content not exceeding substantially 30% by weight.

3. A process as claimed in claim 2 wherein the gas residence time does not exceed substantially two seconds.

4. A process as claimed in claim 3 wherein the temperature ranges from substantially 500° C. to substantially 550° C.

5. A process as claimed in any one of claims 2, 3 or 4 wherein the catalyst has a support with a moderately acidic character and a metal selected from Group VII of the Periodic Table.

6. A process as claimed in any one of claims 2, 3 or 4 wherein the pressure is substantially one atmosphere.

7. A process as claimed in any one of claims 2, 3 or 4 wherein the catalyst has particles with a support material that is thermally and mechanically stable at hydrogasification conditions, said support material having cracking capability for organic molecules and some metal having hydrogenation activity.

8. A process as claimed in claim 4 wherein reacting a portion of the product gas with steam, separating said portion into a hydrogen-rich stream and a carbon monoxide-rich stream, reacting said carbon monoxide-rich stream with steam to yield an additional hydrogen-rich gas stream and recycling said hydrogen-rich gas streams to said reactor.

9. A process as claimed in claim 8 wherein the process further comprises reacting the product gas with steam to yield a mixture of mainly carbon monoxide and hydrogen, separating said mixture into a hydrogen-rich stream and a carbon monoxide-rich stream, recycling said hydrogen-rich stream to said reactor, combining the carbon monoxide-rich stream with the remaining product stream from the steam reforming unit to yield a synthesis gas with a molar ratio of carbon monoxide to hydrogen of approximately one.

10. A process as claimed in any one of claim 2, 3 or 4 wherein the catalyst is γ-alumina, containing at leasta 8% nickel.

11. A process as claimed in any one of claims 2, 3 or 4 wherein the reactor is a fluidized bed reactor.

12. A process as claimed in any one of claims 1, 3 or 4 wherein the biomass has a moisture content not exceeding 20% by weight.

* * * * *